US00PP19830P2

(12) United States Plant Patent
Schram

(10) Patent No.: US PP19,830 P2
(45) Date of Patent: Mar. 17, 2009

(54) ***ZANTEDESCHIA* PLANT NAMED 'SNOW WHITE'**

(50) Latin Name: *Zantedeschia aethiopica*
Varietal Denomination: Snow white

(76) Inventor: Flip Schram, Schram Plants Limited, Royal Oak, Moyvalley, Broadford, County Kildare (IE)

( * ) Notice: Subject to any disclaimer, the term of this patent is extended or adjusted under 35 U.S.C. 154(b) by 0 days.

(21) Appl. No.: 12/072,858

(22) Filed: Feb. 27, 2008

(51) Int. Cl.
*A01H 5/00* (2006.01)

(52) U.S. Cl. ..... Plt./490
(58) Field of Classification Search ..... Plt./490
See application file for complete search history.

*Primary Examiner*—Kent L Bell

(57) ABSTRACT

A new and distinct cultivar of *Zantedeschia* named 'SNOW WHITE' that is distinguishable by dense dwarf habit, medium-green foliage, and large fragrant, white and yellow inflorescences. In combination these traits set 'SNOW WHITE' apart from all other existing varieties of *Zantedeschia* known to the inventor.

3 Drawing Sheets

Genus: *Zantedeschia.*
Species: *aethiopica.*
Denomination: 'SNOW WHITE'.

BACKGROUND OF THE INVENTION

The present invention relates to a new and distinct cultivar of calla lily grown for use in woodland borders and damp grasslands. The new invention from the family Araceae, is known botanically as *Zantedeschia aethiopica* and will be referred to hereinafter by the cultivar name 'SNOW WHITE'.

The new *Zantedeschia* cultivar named 'SNOW WHITE' was discovered in 2003 as a naturally occurring branch sport of *Zantedeschia* 'Crowborough' (unpatented). The inventor discovered 'SNOW WHITE' at the inventor's nursery in County Kildare, Ireland. The parent is an individual *Zantedeschia* 'Crowborough'. The inventor selected 'SNOW WHITE' based on the criteria of plant height and inflorescence size.

*Zantedeschia aethiopica* typically produces a "flower" (inflorescence) consisting of a white spathe and a yellow spadix, although the spadix also has a white surface which is largely obscured by numerous sessile yellow staminate flowers.

The new variety named 'SNOW WHITE' is distinguishable from the parent by plant height. 'SNOW WHITE' grows to only 60 cm. in height whereas 'Crowborough' reaches a height of 100 cm. or more. Plant specimens of smaller stature generally exhibit smaller inflorescences, however 'SNOW WHITE' exhibits large white and yellow inflorescences that are as large as those of the parent.

The distinguishing characteristics of 'SNOW WHITE' are dense dwarf habit, medium-green foliage, and large fragrant white and yellow inflorescences that bloom winter through spring. Mature dimensions when in bloom are 60 cm. in height and 60 cm. in width. Cultural requirements include shade, moist fertile soil, and regular water. 'SNOW WHITE' is hardy to USDA Zone 8.

The first asexual reproduction of 'SNOW WHITE' was accomplished at the inventor's nursery, in County Kildare, Ireland. Asexual propagation was conducted by the inventor using the method of division. Since that time under careful observation 'SNOW WHITE' has been determined fixed, stable and true to type in subsequent generations of asexual propagation.

SUMMARY OF THE INVENTION

The following traits have been repeatedly observed and represent the distinguishing characteristics of the new *Zantedeschia* cultivar named 'SNOW WHITE'. These traits in combination distinguish 'SNOW WHITE' from all other existing varieties of *Zantedeschia* known to the inventor. 'SNOW WHITE' has not been tested under all possible conditions. Phenotypic differences may be observed with variations in environmental, climatic, and cultural conditions without however any variance in genotype.

1. 'SNOW WHITE' exhibits dense dwarf habit.
2. 'SNOW WHITE' exhibits medium-green foliage.
3. 'SNOW WHITE' exhibits large fragrant white and yellow inflorescences.
4. 'SNOW WHITE' is asexually propagated by the method of division.
5. 'SNOW WHITE' reaches 60 cm. in height and 60 cm. in width at maturity.
6. 'SNOW WHITE' is hardy to USDA Zone 8.
7. 'SNOW WHITE' blooms winter through spring.

BRIEF DESCRIPTION OF THE DRAWINGS

The accompanying color drawings illustrate the overall appearance of the new *Zantedeschia* cultivar named 'SNOW WHITE' showing color as true as is reasonably possible to obtain in color reproductions of this type. Color in the drawings may differ from color values cited in the detailed botanical description, which accurately describe the actual color of the new variety 'SNOW WHITE'. The drawings were made from 2 year old plants which had been grown in a frost-protected greenhouse and then outside in County Kildare, Ireland.

Figure 1:
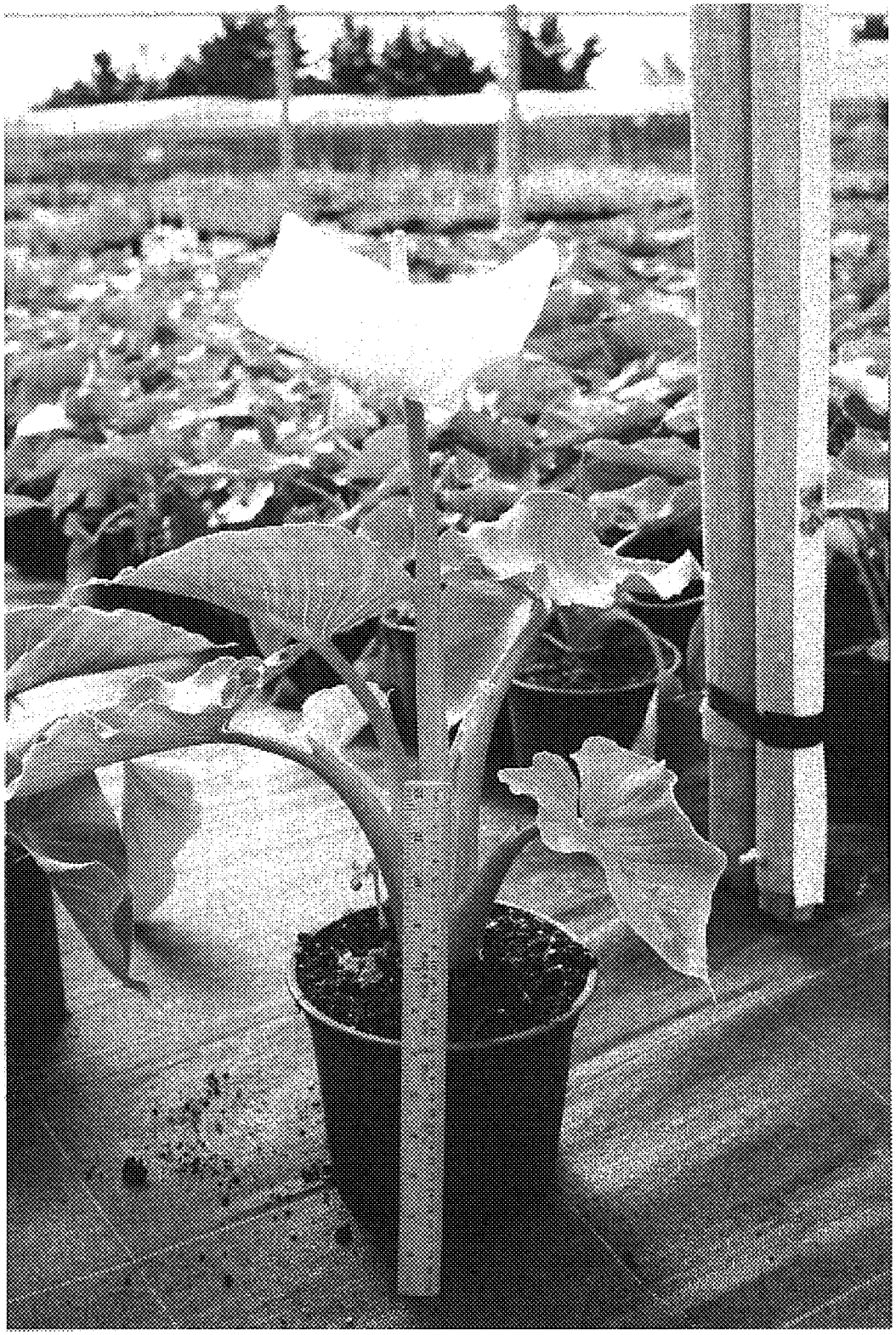
FIG. 1 depicts the entire plant in bloom from a side perspective.
Figure 2:
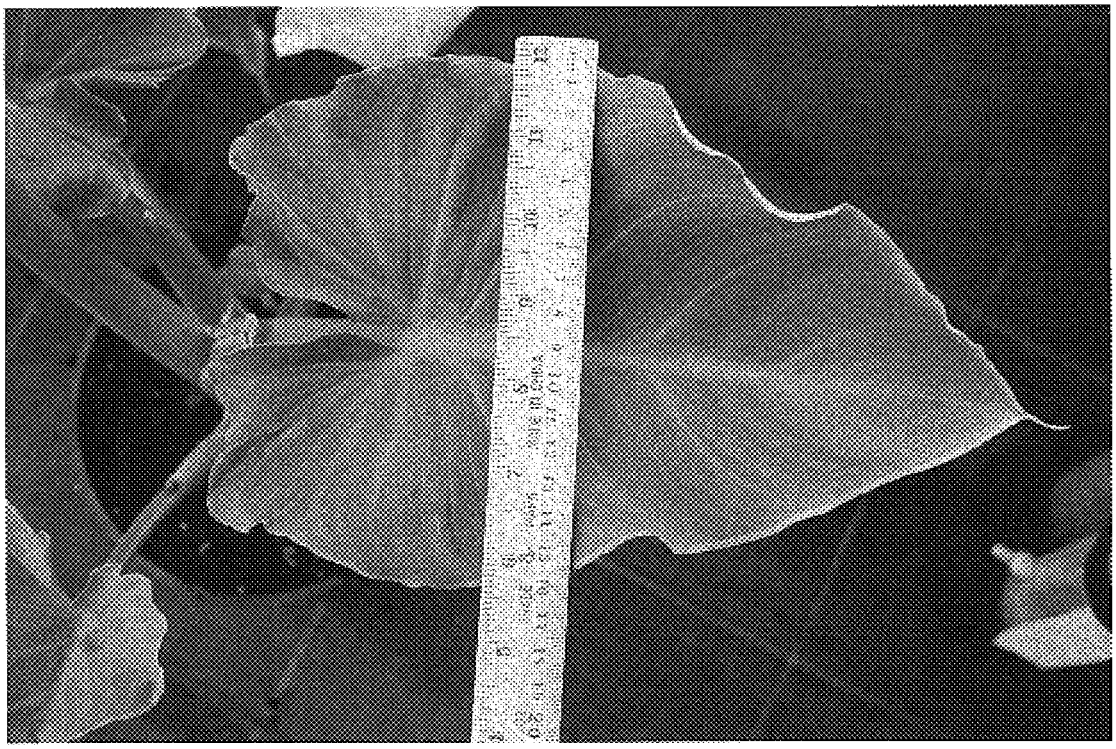
FIG. 2 depicts a close up of a leaf.
Figure 3:
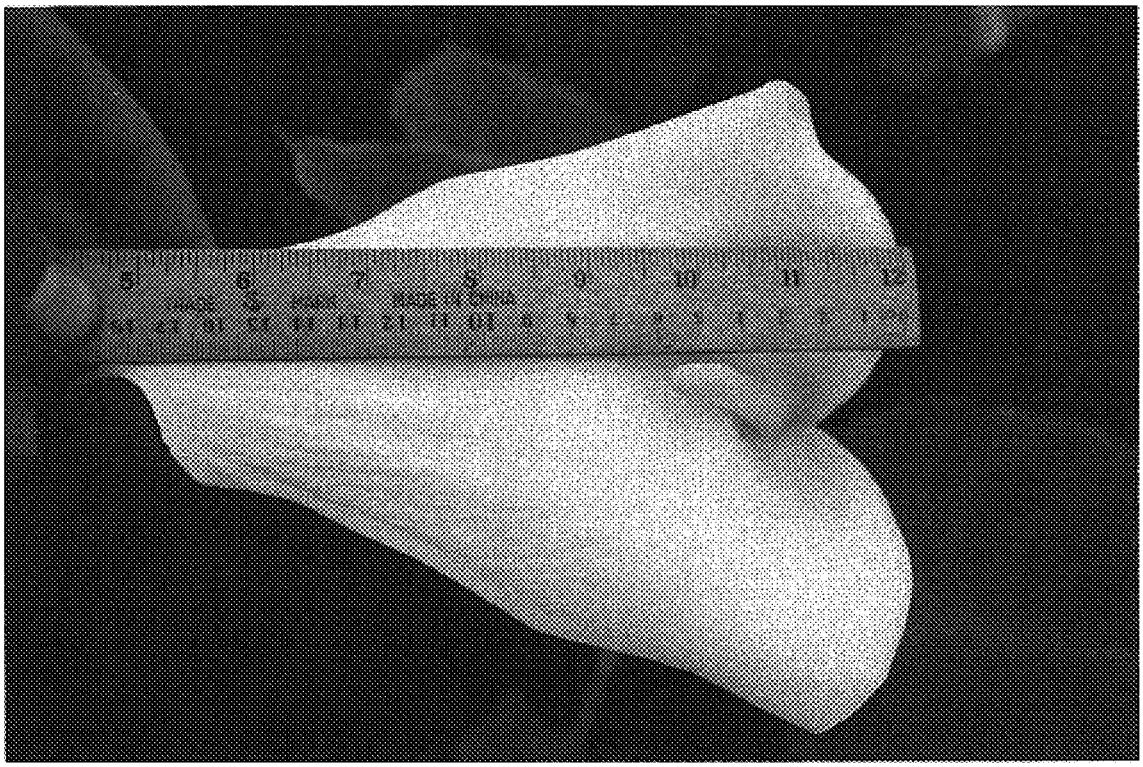
FIG. 3 depicts a close up of a inflorescence.

The drawings were made using conventional techniques and although inflorescence and foliage color may appear different from actual color due to light reflectance they are as accurate as possible by conventional photography.

BOTANICAL DESCRIPTION OF THE PLANT

The following is a detailed botanical description of the new *Zantedeschia* cultivar named 'SNOW WHITE'. Observations, measurements, values and comparisons were collected in Arroyo Grande, Calif. during February of 2008 from 24-month-old plants in 7-litre containers and grown in a frost-protected greenhouse in Watsonville, Calif. Color determinations were made in accordance with the 2001 Royal Horticultural Society Colour Chart from London, England, except where general color terms of ordinary dictionary significance are used. The growing requirements of the new variety are similar to the species.

Botanical classification: *Zantedeschia aethiopica* 'SNOW WHITE'.
Family: Araceae.
Genus: *ZANTEDESCHIA*.
Species: *aethiopica*.
Denomination: 'SNOW WHITE'.
Common name: Calla lily.
Habit: Dense dwarf habit.
Commercial category: Herbaceous perennial.
Use: Woodland border and damp grassland.
Suggested commercial container size: 1-litre container or larger.
Parentage: *Zantedeschia aethiopica* 'SNOW WHITE' was discovered as a naturally occurring branch sport of the following:
*Parent.*—An individual *Zantedeschia* 'Crowborough' (unpatented).
Propagation method: Division.
Rooting system: Fibrous and fleshy.
Vigor: Moderate.
Crop time (average): 6 months to produce a 1-litre container from division.
Temperature (range): The recommended air temperature is 20–21° Centigrade.
Plant dimensions (first year): 60 cm. in height and 40 cm. in width.
Plant dimensions (at maturity): 60 cm. in height and 60 cm. in width.
Cultural requirements: Plant in shade, in moist fertile soil, with regular water.
Pest susceptibility: Susceptible to slugs, snails and aphids.
Disease susceptibility: None known to the inventor.
Hardiness: USDA Zone 8.
Special considerations: All plant parts can elicit dermal irritation if handled.
Foliage:
*Type,*—Evergreen.
*Leaf arrangement.*—Basal.
*Leaf division.*—Simple.
*Leaf margin.*—Entire and undulate.
*Leaf shape.*—Sagittate.
*Leaf length* (*average*).—23 cm.
*Leaf width* (*average*).—13 cm.
*Leaf color* (*abaxial surface*).—N138A.
*Leaf color* (*adaxial surface*).—39A.
*Leaf base.*—Sagittate.
*Leaf apex.*—Caudate.
*Venation pattern.*—Pinate.
*Vein color* (*abaxial and adaxial surfaces*).—N 138C.
*Leaf surfaces* (*abaxial and adaxial*).—Glabrous.
*Leaf attachment.*—Petiolate.
*Petiole length* (*range*).—30–40 cm.
*Petiole width.*—0.75 cm.
*Petiole shape* (*range*).—Plano-convex to sulcate.
*Petiole surface.*—Glabrous.
*Petiole texture.*—Spongy/pithy.
*Petiole color.*—144A.
*Petiole base.*—Sheathing.
*Foliage fragrance.*—None observed.
Inflorescence: The inflorescence consists of a white spathe and spadix. Spadix surface appears yellow by virtue of numerous sessile yellow staminate flowers.
*Inflorescence type.*—Spadiceous.
*Inflorescence quantity* (*average*).—11 per 7-litre container plant.
*Aspect.*—Facing upward and outward.
*Persistent or self-cleaning.*—Persistent.
*Peduncle length* (*range*).—30–40 cm.
*Peduncle width.*—1.50 cm.
*Peduncle shape* (*range*).—Subterete to trigonous.
*Peduncle color.*—138B.
*Peduncle surface.*—Glabrous.
*Peduncle strength.*—Strong.
*Peduncle texture.*—Spongy/pithy.
*Blooming seasons.*—Winter-spring.
*Inflorescence fragrance.*—Sweet perfume fragrance.
*Lastingness of inflorescence* (*range*).—7–14 days.
*Corolla.*—Absent.
*Calyx.*—absent.
*Spathe.*—Number: One per inflorescence. Color (adaxial surface): 155D. Color (abaxial surface): 155D. Surfaces (adaxial and abaxial): Glabrous. Shape: Sub-cylindrical to funnel. Apex: Caudate and recurved. Base: Convolute. Margin: Entire and undulate. Width (range): 2–12 cm. Length: 17 cm.
*Spadix.*—Number: One per inflorescence. Spadix color: 155D. Spadix shape: Sub-cylindrical. Spadix apex: Rounded. Spadix height: 8.50 cm. Spadix diameter: 1.10 cm. Spadix attachment: Sessile. Staminate flower number: >100 from midway of spadix to apex. Staminate flower color: 13B. Staminate flower length (average): 3 mm. Pistillate flower number (average): 60 at base of spadix. Pistillate flower color: 13D. Pistillate flower shape: Columnar. Pistillate flower length: 6 mm. Pollen color: 158A. Pollen quantity: Heavy. Ovary position: Superior. Ovary color: 142D. Ovary shape: Subcylindrical. Ovary dimensions: 1.50 cm. in height and 1 cm. in width.
Seed: None observed to date.

It is claimed:

1. A new and distinct cultivar of *Zantedeschia* plant named 'SNOW WHITE' as described and illustrated herein.

* * * * *